United States Patent
Trinka et al.

(10) Patent No.: US 8,217,200 B2
(45) Date of Patent: Jul. 10, 2012

(54) **PROCESS FOR THE PREPARATION OF 2-CHLOROETHOXY-ACETIC ACID-*N,N*-DIMETHYLAMIDE**

(75) Inventors: Péter Trinka, Budapest (HU); Tibor Mezei, Budapest (HU); József Reiter, Budapest (HU); Ferenc Bartha, Tiszavasvári (HU); Zoltán Katona, Eger (HU); Györgyi Vereczkeyné Donáth, Budapest (HU); Kálmán Nagy, Budapest (HU); László Pongó, Kerepes (HU)

(73) Assignee: Egis Gyogyszergyar Nyilvanosan Mukodo Reszvenytarsasag, Budapest (HU)

( * ) Notice: Subject to any disclaimer, the term of this patent is extended or adjusted under 35 U.S.C. 154(b) by 821 days.

(21) Appl. No.: 12/096,616

(22) PCT Filed: Dec. 8, 2006

(86) PCT No.: PCT/HU2006/000110
§ 371 (c)(1),
(2), (4) Date: Nov. 10, 2008

(87) PCT Pub. No.: WO2007/066164
PCT Pub. Date: Jun. 14, 2007

(65) Prior Publication Data
US 2009/0221853 A1    Sep. 3, 2009

(30) Foreign Application Priority Data
Dec. 8, 2005 (HU) .................................... 0501140

(51) Int. Cl.
*C07C 233/05* (2006.01)
*C07C 231/12* (2006.01)
(52) U.S. Cl. .................................................... 564/201
(58) Field of Classification Search ............... 564/201
See application file for complete search history.

(56) References Cited

U.S. PATENT DOCUMENTS

| | | | | |
|---|---|---|---|---|
| 3,757,008 A | 9/1973 | Hellerbach | | 540/512 |
| 5,331,100 A | 7/1994 | Smith | | 561/468 |
| 6,335,468 B1 | 1/2002 | Hatajima | | 564/133 |
| 6,423,748 B1 * | 7/2002 | Park et al. | | 514/609 |
| 6,562,995 B1 * | 5/2003 | Lan-Hargest et al. | | 560/104 |

FOREIGN PATENT DOCUMENTS

DE      2150075      *    4/1972

OTHER PUBLICATIONS

Kuznetsov et al, Soviet Progress in Chemistry, Allerton Press, Ney York, NY,, US, vol. 44, No. 7,744-747, 1978(Not provide since this reference should be availbale in the PCT report).*
Skinner, W.A. et al; Tick repellents I: Ethylene . . . ; Jour. Pharm. Sciences; vol. 71, No. 7, Jul. 1982; XP002426871; 837-839.
Mitchell J.A. et al; The preparation of Aliphatic . . . ; Jour. Amer. Chem. Soc.; vol. 53; May 1931; XP009001209; 1879-1883.
Kuznetsov N.V. et al; Certain reactions of . . . ; Ukrain Khimiche Zhurnal; vol. 44; No. 7; 1978; XP008076891; 77-80.

* cited by examiner

*Primary Examiner* — Shailendra Kumar
(74) *Attorney, Agent, or Firm* — Jonathan Myers; Andrew Wilford

(57) ABSTRACT

According to the present invention, 2-chloroethoxy-acetic acid-N,N-dimethylamide of the Formula (I) is prepared by reacting 2-hydroxyethoxy-acetic acid-N,N-dimethylamide of the Formula (II) in a solvent optionally in the presence of a catalyst with thionyl chloride and removing the solvent by distillation.

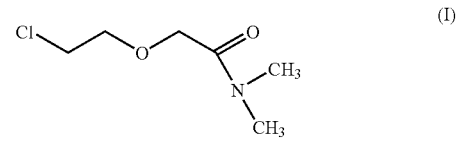

(I)

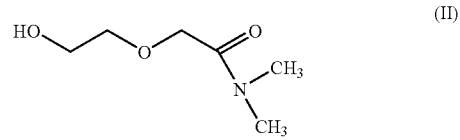

(II)

15 Claims, No Drawings

PROCESS FOR THE PREPARATION OF 2-CHLOROETHOXY-ACETIC ACID-N,N-DIMETHYLAMIDE

CROSS REFERENCE TO RELATED APPLICATIONS

This application is the US national phase of PCT application PCT/HU2006/000110, filed 8 Dec. 2006, published 14 Jun. 2007 as WO 2007/066164, and claiming the priority of Hungarian patent application P0501140 itself filed 8 Dec. 2005, whose entire disclosures are herewith incorporated by reference.

TECHNICAL FIELD OF THE INVENTION

The present invention is related to a process for the preparation of 2-chloroethoxy-acetic acid-N,N-dimethylamide of the Formula (I), an intermediate thereof and process for the preparation of the intermediate.

2-chloroethoxy-acetic acid-N,N-dimethylamide of the Formula (I)

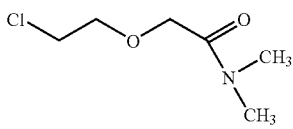

is an intermediate in the manufacture of the antihistamine and antiallergic pharmaceutical active ingredient known by the International Nonproprietary Name cetirizine. Both cetirizine of the Formula (X)

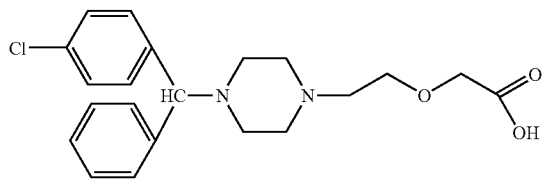

which is chemically (±)-{2-[4-(α-phenyl-p-chlorobenzyl)-piperazin-1-yl]-ethoxy}-acetic acid and the levorotatory enantiomer thereof, (−)-{2-[4-α-phenyl-p-chlorobenzyl)-piperazin-1-yl]-ethoxy}-acetic acid known by the International Nonproprietary Name levocetirizine, are used in the medicine.

TECHNICAL BACKGROUND OF THE INVENTION

Cetirizine of the Formula (X) is prepared according to the state of the art by the hydrolysis of N,N-dimethyl-{2-[4-(α-phenyl-p-chlorobenzyl)-piperazin-1-yl]-ethoxy}-acetamide of the Formula (IX)

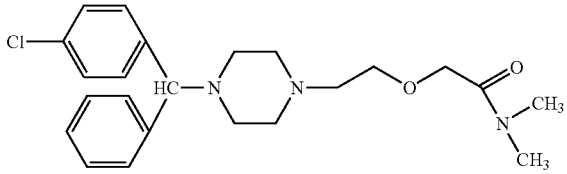

2-Chloroethoxy-acetic acid-N,N-dimethylamide of the Formula (I) is an important intermediate in the preparation of the compound of the Formula (IX) and the compound of the Formula (X) and optical isomers thereof.

A process for the preparation of 2-chloroethoxy-acetic acid-N,N-dimethylamide of the Formula (I) has been disclosed in German Publication Document No. 2 150 075. According to this process, 2-chloroethoxy-acetic acid and aqueous dimethylamine solution are reacted in presence of triethylamine and ethyl-chloroformate and the product 2-chloroethoxy-acetic acid-N,N-dimethylamide is distilled in vacuo. The disadvantage of this process resides in the fact that the cost of the reagents is relatively high as compared to the price of the product, and the purity of the product is not suitable for the purpose of the production of medicines.

Therefore the need arises for a process suitable for the preparation of 2-chloroethoxy-acetic acid-N,N-dimethylamide of the Formula (I) in the purity suitable for use in the production of pharmaceutical active ingredients.

The above objective is solved by the present invention.

SUMMARY OF THE INVENTION

The basis of the present invention is the surprising recognition that 2-chloroethoxy-acetic acid-N,N-dimethylamide of the Formula (I) can be prepared easily and in satisfactory quality for the preparation of pharmaceutical active ingredients by reacting the solution of 2-hydroxyethoxy-acetic acid-N,N-dimethylamide of the Formula (II)

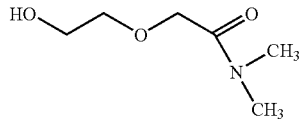

prepared in a halogenated hydrocarbon type or an aromatic solvent and optionally in the presence of a catalyst with thionyl chloride and distilling off the solvent after the reaction. If desired, the product 2-chloroethoxy-acetic acid-N,N-dimethylamide of the Formula (I) can be purified by vacuum distillation.

According to the second aspect of the present invention, there is provided a process for the preparation of the new intermediate 2-hydroxyethoxy-acetic acid-N,N-dimethylamide of the Formula (II).

DETAILED DESCRIPTION OF THE INVENTION

According to the first aspect of the present invention, there is provided a process for the preparation of 2-chloroethoxy-acetic acid-N,N-dimethylamide of the Formula (I), which comprises reacting the solution of 2-hydroxyethoxy-acetic acid-N,N-dimethylamide of the Formula (II) prepared in a halogenated hydrocarbon type or an aromatic solvent and optionally in the presence of a catalyst with thionyl chloride and distilling off the solvent after the reaction.

During the reaction, a halogenated hydrocarbon type or an aromatic solvent, e.g. dichloroethane, carbon tetrachloride, dichloromethane, benzene, toluene or xylene, preferably dichloromethane or toluene can be used.

The reaction is carried out at a temperature between 0 and 40° C., preferably between 10 and 25° C. The reaction time depending upon the reaction temperature is about 0.2 to 4 hours.

As catalyst, an organic base, such as pyridine or triethylamine, preferably pyridine can be used.

The starting compound 2-hydroxyethoxy-acetic acid-N,N-dimethylamide of the Formula (II) is new.

According to the second aspect of the present invention, there are provided processes for the preparation of 2-hydroxyethoxy-acetic acid-N,N-dimethylamide of the Formula (II).

According to the first process variant, dimethylamine of the Formula (IV)

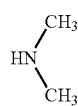

IV is reacted in a suitable solvent with [1,4]-dioxane-2-one of the Formula (III)

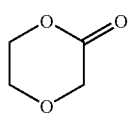

III and the solvent is evaporated. The product 2-hydroxyethoxy-acetic acid-N,N-dimethylamide of the Formula (II) is directly suitable for the preparation of 2-chloroethoxy-acetic acid-N,N-dimethylamide of the Formula (I).

The starting substance of the reaction, [1,4]-dioxane-2-one of the Formula (III) is known compound according to the state of the art (Bull. Soc. Chim. Fr.: 1956, 1210).

Suitable solvents for the reaction are polar or apolar solvents, e.g. dioxane, tetrahydrofurane, toluene, ethanol or acetonitrile. Particularly advantageously dioxane can be used.

The reaction is carried out at a temperature slightly lower than room temperature, advantageously between 5 and 15° C., the most preferably at approximately 5° C.

When the reaction is complete, 2-hydroxyethoxy-acetic acid-N,N-dimethylamide of the Formula (II) is obtained by evaporating the solvent.

According to the second variant, chloroacetic acid-N,N-dimethylamide of the Formula (V)

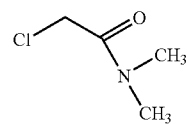

V is reacted with ethylene glycol monosodium salt of the Formula (VI)

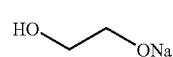

VI in ethylene glycol or N,N-dimethyl-formamide solvent or in the mixture of ethylene glycol and dioxane optionally in the presence of catalyst and the solvent is evaporated.

Suitable catalysts are tetraalkyl-ammonium salts wherein the alkyl group comprises 1 to 6 carbon atoms. Preferably, tetrabutyl ammonium hydroxide can be used.

After the evaporation of the solvent, the product 2-hydroxyethoxy-acetic acid-N,N-dimethylamide of the Formula (II) is directly suitable for transformation into 2-chloroethoxy-acetic acid-N,N-dimethylamide of the Formula (I).

Chloroacetic acid-N,N-dimethylamide of the Formula (V) is known compound according to the state of the art. [(W. E. Weaver, W. M. Whaley: J. Am. Chem. Soc. 69, 516 (1947)].

The solvent of the reaction is used in 5 to 8-fold, preferably 5-fold amount calculated on the basis of the weight of the ethylene glycol monosodium salt.

The reaction is carried out at a temperature between 20 and 80° C., preferably at 50° C. Optionally a tetraalkyl ammonium salt wherein the alkyl group comprises 1 to 6 carbon atoms, e.g. tetrabutyl ammonium hydroxide can be used as catalyst. The amount of the catalyst is between 1 to 25 g, preferably 10 g calculated for each mole of chloroacetic acid-N,N-dimethylamide of the Formula (V).

The work-up of the reaction mixture is carried out by evaporating the solvent.

The third process variant for the preparation of 2-hydroxyethoxy-acetic acid N,N-dimethylamide of the Formula (II) comprises reacting sodium chloroacetate and ethylene glycol monosodium salt in ethylene glycol solvent, and the thus obtained 2-hydroxyethoxy-acetic acid sodium salt of the Formula (VII)

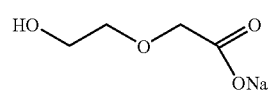

VII is reacted with dimethylamine hydrochloride of the Formula (VIII)

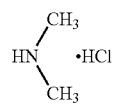

VIII in a suitable solvent or in the melt. The product 2-hydroxyethoxy-acetic acid-N,N-dimethylamide of the Formula (II) obtained by this process variant is suitable for the direct transformation into 2-chloroethoxy-acetic acid-N,N-dimethylamide of the Formula (I) as well.

The starting materials of the reaction are commercially available.

According to a preferable embodiment of the process, 2-hydroxyethoxy-acetic acid sodium salt of the Formula (VII) is not isolated in pure form, since sodium chloride present in the product does not affect the amidation reaction with dimethylamine hydrochloride.

In that case, when the reaction of 2-hydroxyethoxy-acetic acid sodium salt of the Formula (VII) with dimethylamine hydrochloride is carried out in solution, advantageously aromatic hydrocarbon type solvents, preferably toluene can be used. Using such a solvent allows the isolation of the product from the inorganic salt present in the reaction mixture.

After the reaction has completed, the inorganic salts are filtered off and the solvent is evaporated.

Raw 2-hydroxyethoxy-acetic acid-N,N-dimethylamide of the Formula (II) obtained by any of the above-mentioned process variants is directly suitable for the conversion into 2-chloroethoxy-acetic acid-N,N-dimethylamide of the Formula (I).

Further details of the present invention are provided in the following examples without limiting the scope of protection to said examples.

Example 1

2-hydroxyethoxy-acetic acid-N,N-dimethylamide

Into a round-bottom flask of the volume of 100 ml are transferred 50 ml dioxane and the solvent is cooled to 5° C. Subsequently 8.1 g (0.18 mole) dimethylamine is absorbed in the solvent at the temperature of 5-10° C. in 20 minutes. To the solution of dimethylamine, 10.2 g (0.1 mole) of [1,4]-dioxane-2-one are added at the same temperature in 5 minutes and the reaction mixture is stirred at room temperature for 2 hours. After the reaction period, the solvent is evaporated in vacuo at the temperature of 50° C. in one hour. Thus 14.1 g (95.9%) of the title product are obtained, which has the purity of 98% as determined by gas chromatography. Optionally the product can be purified by distilling in vacuo (boiling temperature 130-135° C./13 Pa). The raw product is directly suitable for the preparation of 2-chloroethoxy-acetic acid-N,N-dimethyl-amide.

$^1$H-NMR (CDCl$_3$): δ=2.94 (s), 2.99 (s), 3.6 (m), 3.7 (m), 4.26 (s) ppm.

| Elemental Analysis: | | | |
|---|---|---|---|
| Calculated: | C: 48.96%; | H: 8.90%; | N: 9.52%. |
| Measured: | C: 49.20%; | H: 8.90%; | N: 9.32%. |

Example 2

2-hydroxyethoxy-acetic acid-N,N-dimethylamide

The process of Example 1 is carried out with the difference that instead of dioxane, ethanol is used as solvent. Thus 7.4 g (50.4%) of the product are obtained. The quality of the product is identical to that obtained by the process of Example 1.

Example 3

2-hydroxyethoxy-acetic acid-N,N-dimethylamide

The procedure of Example 1 is carried out with the difference that instead of dioxane, tetrahydrofurane is used as solvent. Yield, 8.8 g (59.8%). The quality of the product is identical in with that of the product obtained by the process of Example 1.

Example 4

2-hydroxyethoxy-acetic acid N,N-dimethylamide

The procedure of Example 1 is followed with the difference that instead of dioxane, toluene is used as solvent and that the evaporation of the solvent is carried out at 80° C. instead of 50° C. in 4 hours. In this case, the yield is 6.0 g (40.6%). The quality of the product is identical with those obtained by the process of Example 1.

Example 5

2-hydroxyethoxy-acetic acid N,N-dimethylamide

The procedure of Example 1 is followed with the difference that instead of dioxane, acetonitrile is used as solvent. Yield 9.0 g (61.4%). The quality of the product is identical with that obtained by the process of Example 1.

Example 6

2-hydroxyethoxy-acetic acid N,N-dimethylamide 40 ml of ethylene glycol and 8.4 g (0.1 mole) ethylene glycol monosodium salt are weighed into a 100 ml round bottom flask. The reaction mixture is heated to 50° C. with stirring and at this temperature, 12.2 g (0.1 mole) of chloroacetic acid N,N-dimethylamide are added dropwise in 1 hour. The reaction mixture is kept at the same temperature for further 1 hour and subsequently submitted to fractionated distillation. The first fraction (boiling temperature approx. 80° C., 260 Pa) comprises the solvent ethylene glycol. The boiling temperature of the product fraction is 130-135° C. (13 Pa). The purity of the product is higher than 98% as determined by gas chromatography.

Yield 9.25 g (62.8%).

Example 7

2-hydroxyethoxy-acetic acid-N,N-dimethylamide

The procedure of Example 6 is followed with the difference that a 1:1 (v/v) mixture of ethylene glycol and dioxane is used. In this case the yield is 6.27 g (42.6%). The purity of the product exceeds 98% as determined by gas chromatography.

Example 8

2-hydroxyethoxy-acetic acid-N,N-dimethylamide

The process of Example 6 is carried out with the difference that instead of ethylene glycol, dioxane is used as solvent and that 1 g of tetrabutylammonium hydroxide are added to the reaction mixture. In this case, the yield is 4.73 g (32.1%) of the title compound having purity higher than 98% as determined by gas chromatography.

Example 9

2-hydroxyethoxy-acetic acid-N,N-dimethylamide

The process according to Example 6 is followed with the difference that instead of ethylene glycol, N,N-dimethyl formamide is used as solvent. In this case, the yield is 5.13 g (34.8%) of the title compound having the purity greater than 98% as determined by gas chromatography.

Example 10

2-hydroxyethoxy-acetic acid-N,N-dimethylamide

The process according to Example 6 is followed with the difference that instead of ethylene glycol, toluene is used as solvent and 1 g tetrabutyl ammonium hydroxide is added to the reaction mixture. The yield is 5.22 g (35.5%) of the title compound having the purity higher than 98% as determined by gas chromatography.

Example 11

2-hydroxyethoxy-acetic acid-N,N-dimethylamide 200.4 g (1 mol) of crude 2-hydroxyethoxy-acetic acid sodium salt prepared from ethylene glycol monosodium salt and 69 weight % sodium chloroacetate are placed into a 1000 ml round bottom flask equipped with stirrer. 81.5 g (1 mole) of commercial dimethylamine hydrochloride having approximately 8 weight % moisture are added. The reaction mixture is heated to the temperature of 130° C. and is kept at this temperature for 20 minutes. After this period, 400 ml of toluene are added to the reaction mixture and by boiling the azeotropic mixture for a period of 16 hours, the water is separated. After cooling the reaction mixture, sodium chloride is filtered off and the crystals are washed twice with 20 ml toluene each. The toluene phases are combined and the product is isolated by evaporating the toluene. Yield 116.2 g (78.9%) of the title compound having the purity greater than 96% by gas chromatography. The product thus obtained is directly suitable for the conversion into 2-chloroethoxy-acetic acid-N,N-dimethylamide.

Example 12

2-chloroethoxy-acetic acid-N,N-dimethylamide 40 ml of dichloromethane are transferred into a round bottom flask of 250 ml volume and 30.0 g (0.2 mol) 2-hydroxyethoxy-acetic acid-N,N-dimethylamide are added. The vessel is cooled on ice and 25.0 g (0.21 mole) of thionyl chloride are added to it dropwise in 10 minutes. The reaction mixture is stirred at room temperature for 20 minutes, and the solvent is evaporated in vacuo (260 Pa) at 50° C. Thus 33.2, g (99%) of title compound are obtained, which has higher purity than 95% by gas chromatographic analysis. Optionally the product can be purified by vacuum distillation (boiling temperature 85-86° C. at 1.3 Pa).

The product thus obtained is suitable for its direct conversion into N,N-dimethyl-{2-[4-(α-phenyl-p-chlorobenzyl)-piperazin-1-yl]-ethoxy}-acetamide and optical isomers thereof.

Example 13

2-chloroethoxy-acetic acid-N,N-dimethylamide

The process of Example 12 is followed with the difference that before the addition of thionyl chloride, 0.5 ml of pyridine are added to the reaction mixture and that the reaction is completed by stirring the reaction mixture for two hours. In this case, the yield is 33.0 g (98%) of the title compound, which has the purity of 96.2% by gas chromatographic analysis. The product thus obtained is directly suitable for transformation into N,N-dimethyl-{2-[4-α-phenyl-p-chlorobenzyl)-piperazin-1-yl]-ethoxy}-acetamide or optical isomers thereof.

Example 14

(2-chloroethoxy)-acetic acid-N,N-dimethylamide

The procedure disclosed in Example 12 is carried out with the difference that toluene is used as solvent and before the addition of thionyl chloride, 1.0 ml of pyridine is added to the reaction mixture. Under these conditions, the yield is 33.0 g (98%) of the title compound having the gas chromatographic purity of 95.8%. The product thus obtained is directly suitable for conversion into N,N-dimethyl-{2-[4-α-phenyl-p-chlorobenzyl)-piperazin-1-yl]-ethoxy}-acetamide or optical isomers thereof.

What is claimed is:

1. A process for the preparation of 2-chloroethoxy-acetic acid-N,N-dimethylamide of the Formula (I),

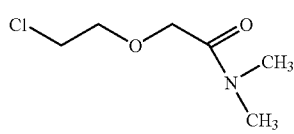

comprising the steps of:
   (a) adding 2-hydroxyethoxy-acetic acid-N,N-dimethylamide of the Formula (II)

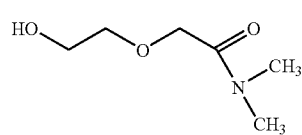

to a solvent, and optionally in the presence of a catalyst, cooling the compound of the Formula (II) with ice; and
   (b) reacting the ice-cooled compound of the Formula (II) with thionyl chloride at a temperature between 10 and 25° C.

2. The process according to claim 1 wherein the solvent is a halogenated hydrocarbon or benzene, toluene or xylene.

3. The process according to claim 1 wherein as catalyst, an organic base is used.

4. 2-hydroxyethoxy-acetic acid-N,N-dimethylamide.

5. A process for the preparation of 2-hydroxyethoxy-acetic acid-N,N-dimethylamide of the Formula (II),

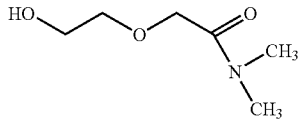

II comprising one of the following alternative process variants:

a) (i) cooling a solvent capable of absorbing dimethylamine of the Formula (IV)

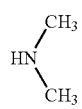

IV to a temperature of 5° C. to form a solution of dimethylamine; and a) (ii) reacting the solution of dimethylamine of the Formula (IV)

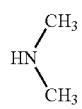

IV prepared in the cooled solvent with [1,4]dioxane-2-one of the Formula (III)

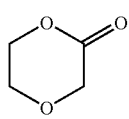

III at a temperature between 5 and 10° C. or b) reacting chloroacetic acid-N,N-dimethylamide of the Formula (V)

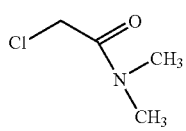

V in ethylene glycol solvent and optionally in the presence of a catalyst with ethylene glycol monosodium salt of the Formula (VI)

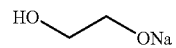

VI or c) reacting dimethylamine hydrochloride of the Formula (VIII)

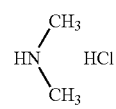

VIII with the sodium salt of 2-hydroxyethoxy-acetic acid of the Formula (VII)

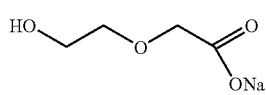

VII and optionally removing water by azeotropic distillation.

6. The variant a) of the process according to claim 5, wherein a polar or apolar solvent is used.

7. The variant a) of the process according to claim 5 wherein according to step a) (ii) the reaction is performed at the temperature of 5° C.

8. The variant b) of the process according to claim 5 wherein as solvent, ethylene glycol, dioxane, toluene, N,N-dimethylformamide or a mixture thereof is used.

9. The process according to claim 8 wherein the solvent is used in a 3 to 8-fold related to the weight of the ethylene glycol monosodium salt.

10. The process variant b) of claim 5 wherein the reaction is carried out at a temperature between 30 and 60° C.

11. The process variant b) according to claim 5, further comprising the step of:
using a tetraalkyl-ammonium salt, wherein the alkyl group comprises 1 to 6 carbon atoms as catalyst.

12. The process according to claim 11 wherein the catalyst is used in 1 to 25 g/mol amount calculated on the basis of the molar amount of chloroacetic acid-N,N-dimethylamide.

13. The process variant c) according to claim 5 wherein as starting material, crude 2-hydroxyethoxy-acetic acid sodium salt containing sodium chloride is used.

14. The process variant c) according to claim 5, in which dimethylamine hydrochloride of the Formula (VIII) and 2-hydroxyethoxy-acetic acid sodium salt of the Formula (VII) in a melt.

15. The process variant c) according to claim 5 wherein the water formed in the reaction is removed by azeotropic distillation with toluene.

* * * * *